United States Patent [19]

Baker et al.

[11] Patent Number: 4,931,451
[45] Date of Patent: Jun. 5, 1990

[54] FUNGICIDAL PYRIDYL SULFENYL CARBAMATES

[75] Inventors: Don R. Baker, Orinda; Francis H. Walker, Mill Valley; Keith H. Brownell, San Jose, all of Calif.

[73] Assignee: ICI Americas Inc., Richmond, Calif.

[21] Appl. No.: 258,409

[22] Filed: Oct. 17, 1988

Related U.S. Application Data

[62] Division of Ser. No. 114,811, Oct. 29, 1987, Pat. No. 4,800,205.

[51] Int. Cl.$^5$ .................. C07D 401/02; A61K 31/44
[52] U.S. Cl. ...................................... 514/335; 546/261
[58] Field of Search ............... 546/261, 265; 514/335, 514/332

[56] References Cited

U.S. PATENT DOCUMENTS 4,672,070 6/1987 Takahashi et al. ................. 546/292

Primary Examiner—Jane T. Fan
Attorney, Agent, or Firm—Michael J. Bradley

[57] ABSTRACT

Novel fungicidal pyridyl sulfenyl carbamates having the formula

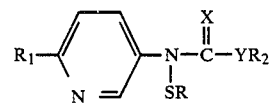

wherein

R is selected from the group consisting of haloalkyl, $C_1$-$C_8$ alkyl, aryl, substituted aryl, arylalkyl, substituted arylalkyl, alkanoyl, alkylamino, arylamino, arylalkylamino and substituted pyridylcarbamoyl;

$R_1$ is $C_1$-$C_3$ alkoxy or $C_1$-$C_3$ haloalkoxy or halomethoxy; alkenyloxy; and halogen;

$R_2$ is $C_1$-$C_3$ alkyl;

X is oxygen or sulfur; and

Y is oxygen or sulfur and fungicidally acceptable organic and inorganic salts thereof which are highly effective fungicides for use both as preventive and curative fungicides are disclosed herein.

5 Claims, No Drawings

FUNGICIDAL PYRIDYL SULFENYL CARBAMATES

This is a divisional of application Ser. No. 114,811, filed Oct. 29, 1987, now U.S. Pat. No. 4,800,205, issued Jan. 24, 1989.

BACKGROUND OF THE INVENTION

Fungal infection of crops such as barley, rice, tomatoes, wheat, beans, roses, grapes and other agriculturally important crops can cause heavy losses in both quantity and quality of agricultural products. It is therefore extremely desirable to have means of preventing, controlling or eliminating fungal growth. Much preventive spraying with commercial fungicides is conducted to attempt to prevent the establishment and growth of fungi on agriculturally important crops. It would also be desirable to have a curative fungicide which, on detection of fungal infestation, could destroy the fungi and eliminate the deleterious effects by use of a post-infection curative spray.

SUMMARY OF THE INVENTION

Novel fungicidal pyridyl sulfenyl carbamates having the formula

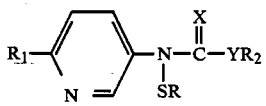

wherein
R is selected from the group consisting of haloalkyl, preferably $C_1$-$C_3$ haloalkyl; $C_1$-$C_8$ alkyl; aryl; substituted aryl; arylalkyl; substituted arylalkyl; alkanoyl, preferably $C_1$-$C_4$ alkanoyl; alkylamino, arylamino, arylalkylamino and substituted pyridyl carboxamidoyl;
$R_1$ is $C_1$-$C_3$ alkoxy or $C_1$-$C_3$ haloalkoxy, preferably methoxy; or halomethoxy; alkenyloxy; and halogen wherein the halogen is chlorine, bromine or fluorine;
$R_2$ is $C_1$-$C_3$ alkyl, preferably methyl;
X is oxygen or sulfur; and
Y is oxygen or sulfur
and fungicidally acceptable organic and inorganic salts thereof which are highly effective fungicides for use both as preventive and curative fungicides are disclosed herein.

The term "fungicide" is used to mean a compound which controls fungal growth. "Controls" includes prevention, destruction and inhibition of fungal growth. The term "curative" is meant to refer to a post-infection application of a fungicide which establishes control of fungal infection and prevents development of deleterious effects of the fungi on the host crop.

DETAILED DESCRIPTION

The novel fungicidal compounds of this invention are fungicidal pyridyl sulfenyl carbamates having the general formula

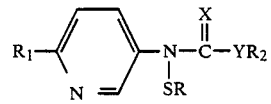

wherein R is selected from the group consisting of haloalkyl, preferably $C_1$-$C_3$ haloalkyl, $C_1$-$C_8$ alkyl, aryl, substituted aryl, arylalkyl wherein the preferred aryl is phenyl, the alkyl is $C_1$-$C_3$ alkyl and the preferred substitutions are Cl, Br, F and nitro, alkanoyl, preferably $C_1$-$C_4$ alkanoyl, alkylamino, arylamino, arylalkylamino, and substituted pyridylcarboxamidoyl, $R_1$ is $C_1$-$C_3$ alkoxy or $C_1$-$C_3$ haloalkoxy preferably methoxy or halomethoxy, alkenyloxy and halogen wherein the halogen is chlorine, bromine or fluorine, $R_2$ is $C_1$-$C_3$ alkyl, preferably methyl, X is oxygen or sulfur, Y is oxygen or sulfur and fungicidally acceptable organic and inorganic salts thereof which are highly effective fungicides for use both as preventive and curative fungicides are disclosed herein.

The compounds of this invention can be generally prepared by a two-step reaction process. The first step comprises reacting the appropriate aminopyridine with the appropriate chloroformate in an inert solvent such as dichloromethane in a suitable reactor. It is desirable to maintain an acid scavenger such as pyridine in the reaction vessel. The reaction generally will proceed at room temperature but will operate at a temperature range from $-30°$ to $80°$ C. The reaction should go to completion within 1 to 3 hours. The resulting product is recovered in a conventional manner by washing with an alkali solution such as sodium hydroxide and water, drying over conventional drying agents such as magnesium sulfate and crystallizing from hexane. The resulting carbamate is then reacted with a properly substituted sulfenyl chloride in an inert solvent in the presence of a tertiary amine such as pyridine or triethylamine, or inorganic base such as sodium hydride (NaH). Salts of the various sulfenylpyridyl carbamates can be conventionally prepared by reacting at least a molar amount of a Lewis acid with the carboxamide. Preferably the reaction is run in a solvent for the carboxamide. The prepared salt is recovered from the reaction mixture by conventional techniques.

Pyridyl sulfenyl carbamates of the invention are basic. The unprotected nitrogen atom of the pyridyl ring can be protonated by an acid, either organic or inorganic. Representative inorganic acids are hydrochloric, nitric, hydrobromic, sulfuric, sulfamic and phosphoric. Representative organic acids are acetic, trifluoroacetic, benzoic, benzenesulfonic, p-toluenesulfonic, naphthalenesulfonic, phenylphosphonic and organophosphonic. The salts so formed are also fungicidal.

EXAMPLE 1

Preparation of O-methyl-N-(2-methoxy-5-pyridyl)-carbamate

5-Amino-2-methoxy pyridine (8.0 grams, 0.064 moles) was dissolved in methylene chloride (100 ml) followed by addition of pyridine (9.5 g, 0.12 mol). To this solution was added methyl chloroformate (8.3 g, 0.088 mol) dropwise with stirring at approximately 15° C. The addition was exothermic and the reaction was stirred for a further two hours at room temperature. It was then washed with water (2 times), dried over magnesium sulfate, filtered, and evaporated in vacuo to yield an orange solid that was triturated with hexane several times to yield 9.3 g, m.p. 100°–101° C. of the title compound as identified by its infrared (IR), nuclear magnetic resonance (NMR) spectra and by mass spectroscopic (MS) analysis. This product was used as an intermediate to produce the novel compounds of Examples 2–4.

EXAMPLE 2

Preparation of Methyl-N-(benzylmethylaminosulfenyl)-N-(2-methoxy-5-pyridyl)-carbamate O-Methyl-N-(2-methoxy-5-pyridyl)-carbamate (5.0 g, 0.027 mol) was added in portions to a stirred mixture of sodium hydride (0.7 g, 0.027 mol) suspended in a solution of tetrahydrofuran (100 ml) and dimethylsulfoxide (10 ml). There was a moderate exotherm and a gas was evolved. The reaction solution was cooled to −65° C. and benzylmethylamino sulfenyl chloride (5.1 g, 0.027 mol) was slowly added. The temperature was allowed to rise to room temperature. The mixture was diluted with water (200 ml) and extracted with methylene chloride (100 ml). This extract was washed with saturated sodium chloride solution, dried over anhydrous magnesium sulfate, filtered and evaporated in vacuo to give 8.8 g of crude product. This was extracted with hexane and flash chromatographed on florisil to give 2.0 g of the title product as an oil, $n_D^{30}$ 1.5460.

EXAMPLE 3

Preparation of O-Methyl-N-trichloromethanesulfenyl-N-(2-methoxy-5-pyridyl)-carbamate O-Methyl-N-(2-methoxy-5-pyridyl)-carbamate (5.0 g, 0.027 moles) was added in portions to a stirred mixture of sodium hydride (0.7 g, 0.027 mol) in dry tetrahydrofuran (80 ml). Hydrogen gas was evolved. After 30 minutes, the stirred suspension was cooled to −50° C. and trichloromethanesulfenyl chloride (5.0 g, 0.027 mol) dissolved in dry tetrahydofuran (5 ml) was added slowly. At the completion of the addition, cooling was discontinued and the mixture was allowed to come to room temperature. The reaction mixture was stirred for 2 hours at room temperature and diluted with methylene chloride (150 ml) and washed with brine (2×100 ml), dried over magnesium sulfate, filtered and evaporated in vacuo to yield 7.7 g of crude product. This was further purified by extraction with hexane and filtration through a bed of florisil, giving 2.1 g of the title product, m.p. 48.0°–55.0° C.

EXAMPLE 4

Preparation of Sulfenyl N,N'-bis-[O-methyl-N-(2-methoxy-5-pyridyl)-carbamate]

O-Methyl-N-(2-methoxy-5-pyridyl)-carbamate (5.0 g, 0.027 mol) was added portion-wise to a stirred suspension of sodium hydride (0.7 g, 0.027 mole) in dry tetrahydrofuran (100 ml) at room temperature. This reaction mixture was cooled to −50° C. and sulfur dichloride (2.8 g, 0.027 mol) was added with stirring. Cooling was discontinued and the temperature allowed to rise to room temperature and stirred for 90 minutes. The reaction was diluted with methylene chloride (100 ml) and washed with water (100 ml) and brine (100 ml). The organic phase was dried over magnesium sulfate, filtered and evaporated in vacuo to give 5.2 grams of a viscous oil which solidifed on trituration with hexane to give 3.9 g of the title product, m.p. 89°–94° C.

Representative compounds of this invention and their properties are shown in Table I.

TABLE I $$R_1 \underset{N}{\overset{}{\diagdown}} \text{—N(SR)—C(=X)—YR}_2$$

| Cmpd. No. | R | $R_1$ | $R_2$ | X | Y | Physical Properties Melting Point $n_D^{30}$ or RF |
|---|---|---|---|---|---|---|
| 1 | —CCl₃ | —OCH₃ | —CH₃ | O | O | 48.0–55.0° C. |
| 2 | —C₆H₄Cl (p-chlorophenyl) | —OCH₃ | —CH₃ | O | O | 49.0–55.0° C. |
| 3 | —CCl₃ | —Cl | —CH₃ | O | S | solid |
| 4 | —CCl₃ | —Cl | —CH₃ | O | O | 57.0–60.0° C. |
| 5 | —C₆H₄NO₂ (o-nitrophenyl) | —OCH₃ | —CH₃ | O | O | 90.0–95.0° C. |
| 6 | —C₆H₃(NO₂)₂ (2,4-dinitrophenyl) | —OCH₃ | —CH₃ | O | O | 120.0–123.0° C. |
| 7 | —N(C₄H₉)₂ | —OCH₃ | —CH₃ | O | O | 1.5129 |

TABLE I-continued $$R_1 \underset{N\,=}{\overset{}{\diagdown}} \overset{}{\underset{SR}{\diagup}} N - \overset{X}{\underset{\|}{C}} - YR_2$$

| Cmpd. No. | R | R₁ | R₂ | X | Y | Physical Properties Melting Point $n_D^{30}$ or RF |
|---|---|---|---|---|---|---|
| 8 | (pyridine with OCH₃) —N—COCH₃ (\|\|O) | —OCH₃ | —CH₃ | O | O | 89.0–94.0° C. |
| 9 | —N(CH₃)—CH₂—phenyl | —OCH₃ | —CH₃ | O | O | 1.5460 |

EXAMPLE 5

Preventative Spray Evaluation Procedures

Barley Powdery Mildew (BPM)

Northrup King Sunbar 401 barley seed is planted (12 seeds/2″ pot) in a sandy-loam soil seven days prior to testing. The test compound is diluted in a 50/50 acetone/water solution to produce concentrations decreasing from 750 ug/ml. The test solution is then sprayed onto the barley plants with atomizing sprayers.

Twenty-four hours later, test plants are placed in an inoculation box equipped with a circulating fan. Barley plants with heavily sporulating *Erysiphe graminis* lesions are placed in front of the fan to dislodge and distribute the spores. After two minutes the fan is shut off and the chamber is left closed five minutes for the spores to settle. Inoculated plants are then placed on an automatic sub-irrigation greenhouse bench.

Results are recorded seven days following inoculation as percent disease control based on the percent reduction in infected area as compared to the untreated control plants. Compound concentrations which provide 90% disease control (EC 90) are determined from dosage/dilution curves.

Leaf Rust (LR)

Seven seeds of Anza wheat are planted in 2″ pots in a sandy-loam soil 12 days prior to testing. The compound to be tested is diluted with a 50/50 acetone/water solution to produce concentrations decreasing from 750 ug/ml. Twelve ml of test solution are sprayed onto the wheat plants with an atomizing sprayer.

A suspension of *Puccinia recondita* urediospores is prepared by vacuuming spores from wheat leaves with ureida pustules and suspending 10⁵ spores/ml in deionized water plus 0.5% Tween® 20 (polyoxyethylene sorbitan monolaurate). Plants are inoculated 24 hours after treatment by spraying with the spore suspension to run-off, allowing it to dry on the leaves, respraying to runoff, and then placing the plants into a mist chamber. Following 48 hours in the mist, plants are moved to a subirrigation greenhouse bench.

Results are recorded ten days following inoculation as percent disease control based on the percent reduction in lesion area as compared to the untreated control plants. Compound concentrations which provide 90% disease control (EC 90) are determined from dosage/dilution curves.

Botrytis Blight (BB)

Two white rose petals are placed in a petri dish lined with wet filter paper. The compound to be tested is diluted with a 50/50 acetone/water solution to produce concentrations decreasing from 750 ug/ml. One half ml of test solution is atomized onto the petals and allowed to dry.

Inoculum is prepared by adding a 5 mm plug from a two-week old *Botrytis cinerea* culture grown on Elliot's V-8 agar, to 10 ml sterile distilled water plus 0.5 ml grape juice. A 20 ul drop of this inoculum suspension is placed on each petal. Petri dishes with inoculated petals are stored in sealed plastic boxes to maintain saturated humidity.

Results are read four days following inoculation as a percent reduction in necrotic area compared to the acetone/water controls. Compound concentrations which provide 90% disease control (EC 90) are determined from dosage/dilution curves.

The results are presented in Table II as an approximate EC 90 in parts per million. 750 ppm equals 750 ug/ml. Partial control at 750 ppm (less than 90%) is indicated by (750). An asterisk (*) indicates no control at 750 ppm.

TABLE II

| Cmpd. No. | BPM | LR | BB |
|---|---|---|---|
| 1 | * | * | 80 |
| 2 | * | * | 50 |
| 3 | (750) | 750 | * |
| 4 | (750) | 750 | * |
| 5 | (750) | (750) | 250 |
| 6 | (750) | * | 250 |
| 7 | (750) | * | 150 |
| 8 | (750) | (750) | 80 |
| 9 | (750) | (750) | 250 |

The compounds of the present invention are useful as fungicides, especially as preventative or curative fungicides, and can be applied in a variety of ways at various concentrations. In general, these compounds and formulations of these compounds can be applied directly to the crop foliage, the soil in which the crop is growing or in the irrigation water for the crop or soil. In practice, the compounds herein defined are formulated into fungicidal compositions, by admixture, in fungicidally effective amounts, with the adjuvants and carriers normally employed for facilitating the dispersion of active ingredients for agricultural applications, recognizing the fact that the formulation and mode of application of a toxicant may affect the activity of the materials in a given application. Thus, these active fungicidal compounds may be formulated as wettable powders, as emulsifiable concentrates, as powdery dusts, as solutions or as any of several other known types of formulations, depending upon the desired mode of application. Preferred formulations for preventative or curative fungicidal applications are wettable powders and emulsifiable concentrates. These formulations may contain as little as about 0.1% to as much as about 95% or more by weight of active ingredient. A fungicidally effective amount depends upon the nature of the seeds or plants to be treated and the rate of application varies from about 0.05 to approximately 25 pounds per acre, preferably from about 0.1 to about 10 pounds per acre.

Wettable powders are in the form of finely divided particles which disperse readily in water or other dispersants. The wettable powder is ultimately applied to the plants either as a dry dust or as a dispersion in water or other liquid. Typical carriers for wettable powders include Fuller's earth, kaolin clays, silicas and other readily wet organic or inorganic diluents. Wettable powders normally are prepared to contain about 5% to about 95% of the active ingredient and usually also contain a small amount of wetting, dispersing, or emulsifying agent to facilitate wetting and dispersion.

Dry flowables or water dispersible granules are agglomerated wettable powders made by either pan granulation or by fluidized bed. The dry flowable is ultimately applied to the plants as a dispersion in water or other liquid. These granules are dust-free and free flowing when dry and yet upon dilution in water, form homogeneous dispersions. Typical carriers for dry flowables include fuller's earth, kaolin clays, silicas and other readily wet organic or inorganic diluents. The dry flowables normally are prepared to contain from about 5% to about 95% of the active ingredient and usually contain a small amount of wetting, dispersing or emulsifying agent to facilitate wetting and dispersion.

Emulsifiable concentrates are homogeneous liquid compositions which are dispersible in water or other dispersant, and may consist entirely of the active compound with a liquid or solid emulsifying agent, or may also contain a liquid carrier, such as xylene, heavy aromatic naphtha, isophorone and other non-volatile organic solvents. For fungicidal application, these concentrates are dispersed in water or other liquid carrier and normally applied as a spray to the area to be treated. The percentage by weight of the essential active ingredient may vary according to the manner in which the composition is to be applied, but in general comprises about 0.1% to 95% of active ingredient by weight of the fungicidal composition.

Typical wetting, dispersing or emulsifying agents used in agricultural formulations include, for example, the alkyl and alkylaryl sulfonates and sulfates and their sodium salts; polyhydroxy alcohols; and other types of surface-active agents, many of which are available in commerce. The surface-active agent, when used, normally comprises from 0.1% to 15% by weight of the fungicidal composition.

Dusts, which are free-flowing admixtures of the active ingredient with finely divided solids such as talc, clays, flours and other organic and inorganic solids which act as dispersants and carriers for the toxicant, are useful formulations for many applications.

Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected.

| EXAMPLES OF TYPICAL FORMULATIONS | | | |
|---|---|---|---|
| Oil | | | |
| Ingredient | | Weight % | |
| Compound 1 | | 1 | |
| Oil solvent-heavy aromatic naphtha | | 99 | |
| Total | | 100 | |
| Emulsifiable Concentrate | | | |
| Compound 1 | | 50 | |
| Kerosene | | 45 | |
| Emulsifying agent (mixture of long chain ethoxylated polyethers with long chain sulfonate) | | 5 | |
| Total | | 100 | |
| Emulsifiable Concentrate | | | |
| Compound 1 | | 90 | |
| Kerosene | | 5 | |
| Emulsifying agent (mixture of long chain ethoxylated polyethers with long chain sulfonate) | | 5 | |
| Total | | 100 | |
| Dusts and/or Powders | | | |
| Ingredient | Wt. % | Wt. % | Wt. % |
| Compound 1 | 0.5 | 50.0 | 90.0 |
| Attapulgite Clay Powder | 93.5 | 44.0 | 4.0 |
| Sodium lignin sulfonate | 5.0 | 5.0 | 5.0 |
| Sodium dioctyl sulfosuccinate | 1.0 | 1.0 | 1.0 |
| Total | 100.0 | 100.0 | 100.0 |

Other useful formulations for fungicidal applications include simple solutions of the active ingredient in a dispersant in which it is completely soluble at the desired concentration, such as acetone, alkylated naphthalenes, xylene and other organic solvents. Pressurized sprays, typically aerosols, wherein the active ingredient is dispersed in finely divided form as a result of vaporization of a low boiling dispersant solvent carrier, such as the Freons, may also be used.

The fungicidal compositions of this invention are applied to the plants in the conventional manner. Thus, the dust and liquid compositions can be applied to the plant by the use of power-dusters, boom and hand sprayers and spray dusters. The compositions can also be applied from airplanes as a dust or a spray because they are effective in low dosages.

We claim:

1. A compound having the structural formula

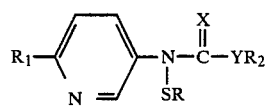

wherein
R is

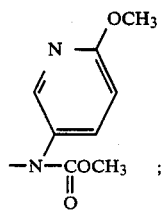

$R_1$ is selected from the group consisting of $C_1$-$C_3$ alkoxy, $C_1$-$C_3$ haloalkoxy and halogen;
$R_2$ is $C_1$-$C_3$ alkyl;
X is oxygen or sulfur; and
Y is oxygen or sulfur
or a fungicidally acceptable organic or inorganic salt thereof.

2. The compound of claim 1 wherein $R_1$ is —OCH$_3$, $R_2$ is —CH$_3$, X is 0 and Y is 0.

3. A fungicidal composition comprising a fungicidally effective amount of a compound having the structural formula

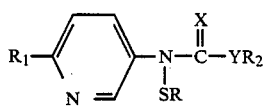

where
R is

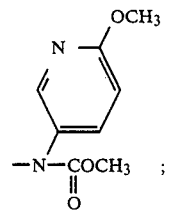

$R_1$ is selected from the group consisting of $C_1$-$C_3$ alkoxy, $C_1$-$C_3$ haloalkoxy and halogen;
$R_2$ is $C_1$-$C_3$ alkyl;
X is oxygen or sulfur; and
Y is oxygen or sulfur
or a fungicidally acceptable organic or inorganic salt thereof in admixture with a diluent or carrier therefor.

4. The method of controlling fungi comprising applying to the area where control is desired a fungicidally effective amount of a compound having the formula

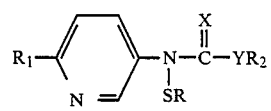

where
R is

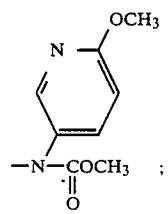

$R_1$ is selected from the group consisting of $C_1$-$C_3$ alkoxy, $C_1$-$C_3$ haloalkoxy and halogen;
$R_2$ is $C_1$-$C_3$ alkyl;
X is oxygen or sulfur; and
Y is oxygen or sulfur or a fungicidally acceptable organic or inorganic salt thereof.

5. The method of claim 4 wherein $R_1$ is —OCH$_3$, $R_2$ is —CH$_3$, X is 0 and Y is 0.

* * * * *